United States Patent [19]

Holtkamp

[11] Plant 5,021

[45] Apr. 5, 1983

[54] AFRICAN VIOLET PLANT

[76] Inventor: Reinhold Holtkamp, Werther Strasse 112, 4294 Isselburg, Fed. Rep. of Germany

[21] Appl. No.: 300,517

[22] Filed: Sep. 9, 1981

[51] Int. Cl.[3] ..... A01H 5/00
[52] U.S. Cl. ..... Plt./69
[58] Field of Search ..... Plt./69

*Primary Examiner*—Robert E. Bagwill

*Attorney, Agent, or Firm*—Schwartz, Jeffery, Schwaab, Mack, Blumenthal & Koch

[57] ABSTRACT

An African violet plant known by the cultivar name Improved Maine and characterized by its profuse blooming habit, with 10 or more flower stems carrying up to 9–12 or more flowers per stem, each of which is basically white, but tipped with blue. Improved Maine blooms essentially continuously, as is further characterized by its compact, uniform and vigorous growth habit. An attractive saleable plant is provided within 8–9 weeks after potting.

1 Drawing Figure

The present invention comprises a new and distinct cultivar of African violet plant, botanically known as *Saintpaulia ionantha,* and hereinafter referred to by the cultivar name Improved Maine.

The new cultivar was referred to during the breeding and selection process by the designation d 240/4, and is a product of a planned breeding program. The basic objective of the breeding program was to create a new African violet cultivar having a white flowered tipped or tinged with blue. Essentially pure white, star-shaped flowers are shown in my U.S. Plant Pat. No. 4,350, granted Dec. 19, 1978, for the cultivar name Maine. The purpose of the present breeding program was to obtain a variety having the same white color, with blue tipping or tinging.

The new cultivar was originated from a cross made in a controlled breeding program in Isselburg, West Germany. The female, or seed parent was a cultivar designated b 1287 blue-white star. The male, or pollen parent was a cultivar designated 26 Z.

The new cultivar Improved Maine was discovered and selected by me as a flowering plant within the progeny of the stated cross in a controlled environment in Isselburg, West Germany. Asexual reproduction of the new cultivar by leaf cuttings and by division of shoots, as performed by me at Isselburg, West Germany, has demonstrated that the combination of characteristics as herein disclosed for the new cultivar are firmly fixed and are retained through successive generations of asexual reproduction.

Improved Maine has not been observed under all possible environmental conditions. The phenotype may vary significantly with variations in environment such as temperature, light intensity and day length. The following observations, measurements and values describe the new cultivar as grown in Isselburg, West Germany, under greenhouse conditions which closely approximate those generally used in commercial practice.

The following traits have been repeatedly observed and are determined to be basic characteristics of Improved Maine, which in combination distinguish this African violet as a new and distinct cutlivar:

1. Compact growth habit.
2. Profuse blooming; 10 or more flower stems with 9–12 or more flowers per stem.
3. Single flowers with occasional additional petal.

4. White flower color, but tipped with blue.
5. Uniform in growth.
6. Attractive saleable plant within 8–9 weeks; in full bloom 10–11 weeks after potting.
7. Vigorous grower.
8. Blooms essentially continuously.

The accompanying photographic drawing shows a typical specimen plant of the new cultivar. The colors appearing in the photograph are as true as possible with color illustrations of this type.

In the following description, color references are made to the Horticultural Colour Chart (HCC) issued by Wilson Colour Ltd., except where general colors of ordinary significance are referred to. Color values were taken under natural light conditions approximately midday in Isselburg, West Germany.

Botanical classification: *Saintpaulia ionantha,* Ramat. cv. Improved Maine.

Parentage:
- *Male parent.*—26 Z.
- *Female parent.*—b 1287 blue-white star.

Propagation: The new cultivar holds its distinguishing characteristics through successive propagations by leaf cuttings and by division of shoots.

Plant: From 8 cm. to 10 cm. tall when grown in pots, and approximately 24–25 cm. in diameter when fully grown.

Leaves:
- *General form.*—Heart-shaped.
- *Diameter.*—60 mm.
- *Texture.*—Soft and hairy.
- *Aspect.*—Velvety, slightly shiny.
- *Veins.*—Upperside visible; underside well-pronounced, light green and shiny.
- *Color (upperside).*—HCC parsley green 00962.
- *Color (underside).*—HCC sage green 000861/2.
- *Petiole.*—Bright green and hairy.

Flowers:
- *Buds.*—Ball-shaped; 6 mm. just before opening; 9–12 or more per stem.
- *Sepals.*—Color: Light green. Calyx: Funneled, flat. Aspect: Spear-shaped. Peduncle: Short, upright, brownish.

Individual flowers:
- *Size.*—40–50 mm.

*Color.*—Upperside: Distinct white with Victoria violet, shades 738/3-0. Underside: Creamy white with shades of violet.

*Borne.*—Flower stem carries 9–12 or more flowers on normal peduncles; flowers tend to tilt down, and occasionally display an additional small petal in center of bloom, or even an extra petal.

*Shape.*—Conventional (2 small and 3 large petals).

*Flowering time.*—First flowers appear 7–8 weeks after potting; after 10–11 weeks full flowering saleable plant.

Reproductive organs:

*Stamens.*—2–3 anthers, composed of 2 cells, with seed capsule slightly pushed through.

*Anthers.*—HCC sulphur yellow 1/2.

*Filaments.*—3 mm. long; yellowish green.

*Styles.*—6 mm. glossy purple with white sigma; base of ovary bright green and hairy.

*Pollen color.*—HCC sulphur 1/3.

Roots: White when young and active; greenish brown when older; normally developed.

Disease resistance: Good as experienced to date.

General observations: Improved Maine is a vigorous grower with a profuse loose corolla of white blossoms tipped with blue. The older flower stems tend to tilt sidewards to make room for younger stems coming from center. This variety blooms almost continuously, and its flowers are long-lasting and non-dropping.

I claim:

1. A new cultivar of African violet known by the cultivar name Improved Maine and characterized by the combined features of profuse blooming habit, with ten or more flower stems carrying up to 9–12 or more flowers per stem, with the flowers being basically white but tipped with blue; single flower form, with an occasional additional petal, frequently in the center; uniform, compact and vigorous growth habit, essentially continuous blooming, and by its ability to provide an attractive saleable plant within 8–9 weeks after potting.

* * * * *

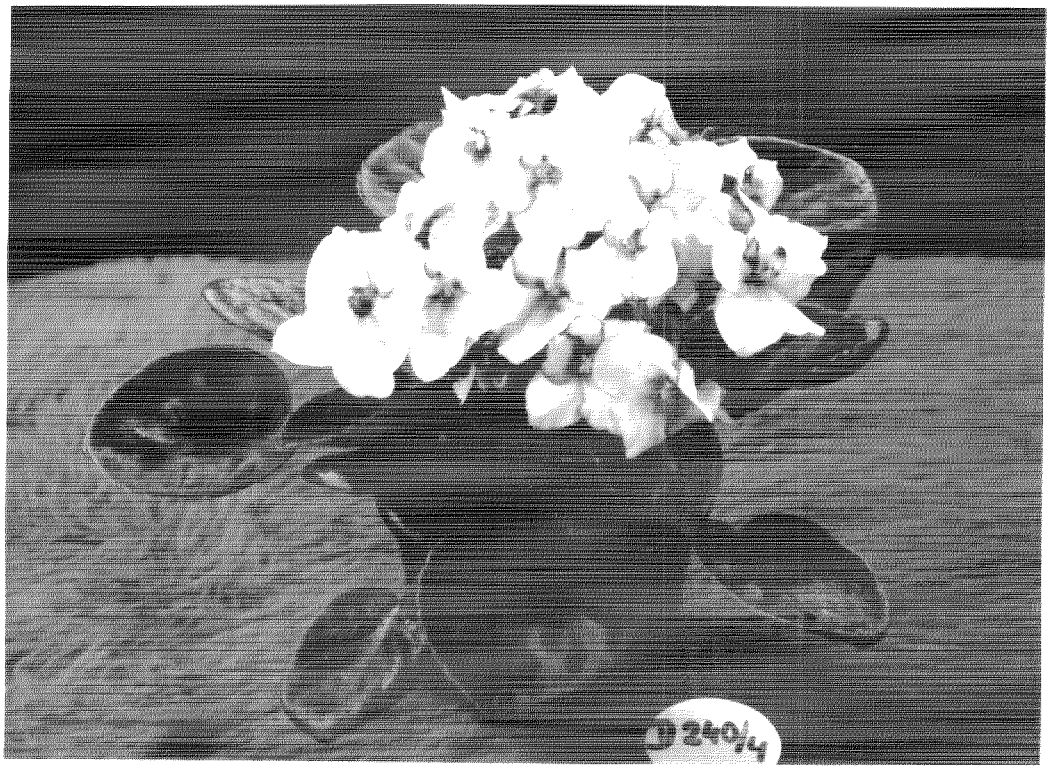
240/4